United States Patent [19]
Holloway

[11] Patent Number: 4,936,448
[45] Date of Patent: Jun. 26, 1990

[54] CATHETER BOWL

[75] Inventor: Joan Holloway, Memphis, Tenn.

[73] Assignee: Vollrath Group, Inc., Gallaway, Tenn.

[21] Appl. No.: 236,028

[22] Filed: Aug. 24, 1988

[51] Int. Cl.$^5$ ............................................. B65D 83/10
[52] U.S. Cl. .................................... 206/364; 206/519
[58] Field of Search ......................... 604/364, 515, 519

[56] References Cited

U.S. PATENT DOCUMENTS

| | | | |
|---|---|---|---|
| 2,858,041 | 10/1958 | Robinson | 220/90.4 |
| 3,339,786 | 9/1967 | Biglin | 220/44 |
| 3,643,830 | 2/1972 | Kinney | 220/44 R |
| 3,670,922 | 6/1972 | Phillips | 220/97 C |
| 3,851,649 | 12/1974 | Villari | 128/275 |
| 4,024,951 | 5/1977 | Green | 206/519 X |
| 4,096,947 | 6/1978 | Morse | 206/519 |
| 4,160,505 | 7/1979 | Rauschenberger | 206/571 |
| 4,216,860 | 8/1980 | Heimann | 206/370 |
| 4,226,328 | 10/1980 | Beddow | 206/364 |
| 4,501,363 | 2/1985 | Isbey, Jr. | 206/570 |

OTHER PUBLICATIONS

Enclosed photograph of Baxter Hospital Supply Device (no date).
Enclosed photograph of Alpha Industries device (no date).

Primary Examiner—Allen M. Ostrager
Attorney, Agent, or Firm—Olson & Hierl

[57] ABSTRACT

A bowl for storing tubing such as a catheter is provided. The bowl includes a bottom wall and a side wall having an inner surface formed integrally with the bottom wall. The side wall extends generally perpendicularly from the bottom wall. An inwardly extending retaining member is integrally provided on the inner surface of the side wall to retain the catheter in the bowl. In a preferred embodiment, the bowl is nestable with similar bowls.

27 Claims, 2 Drawing Sheets

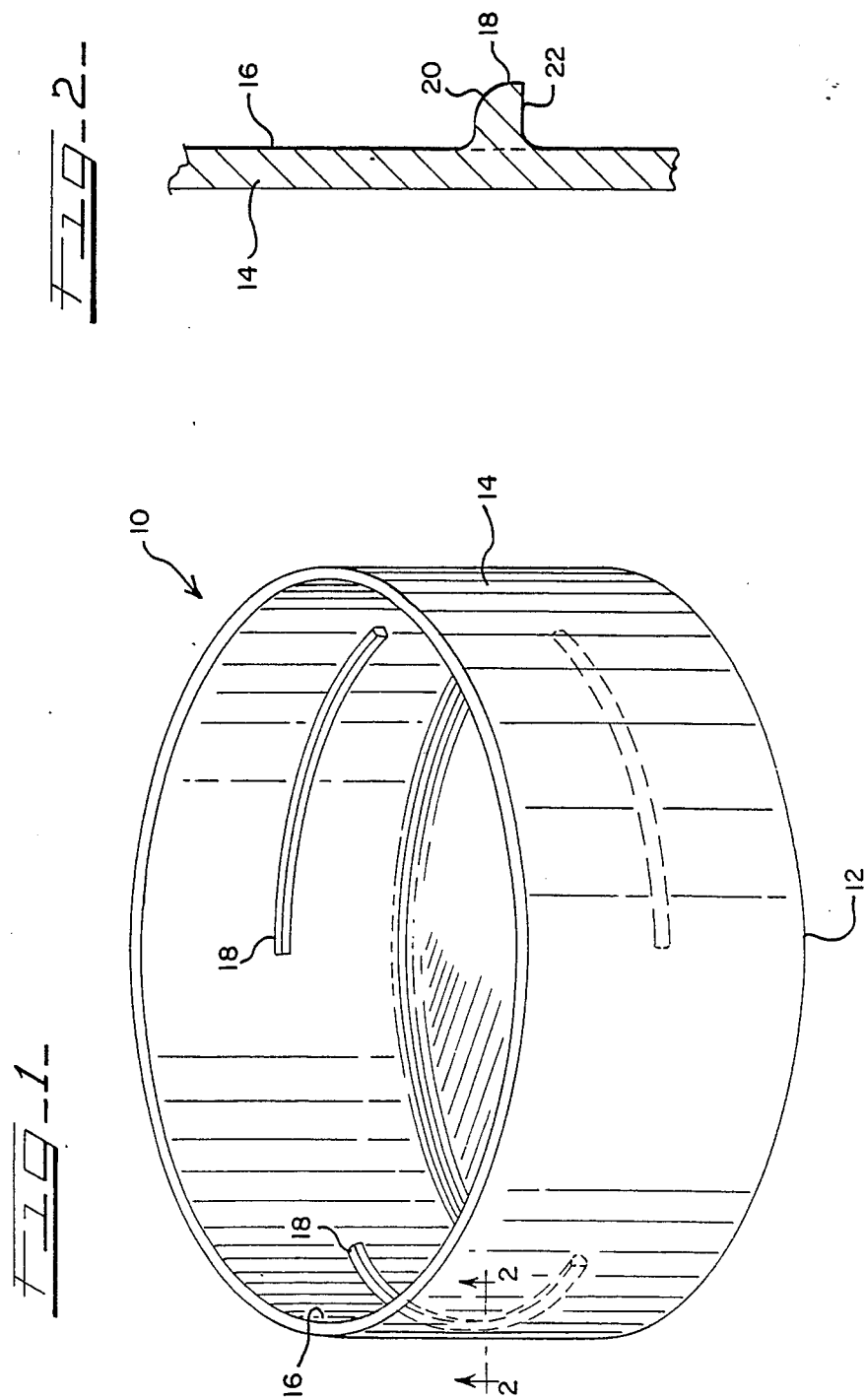

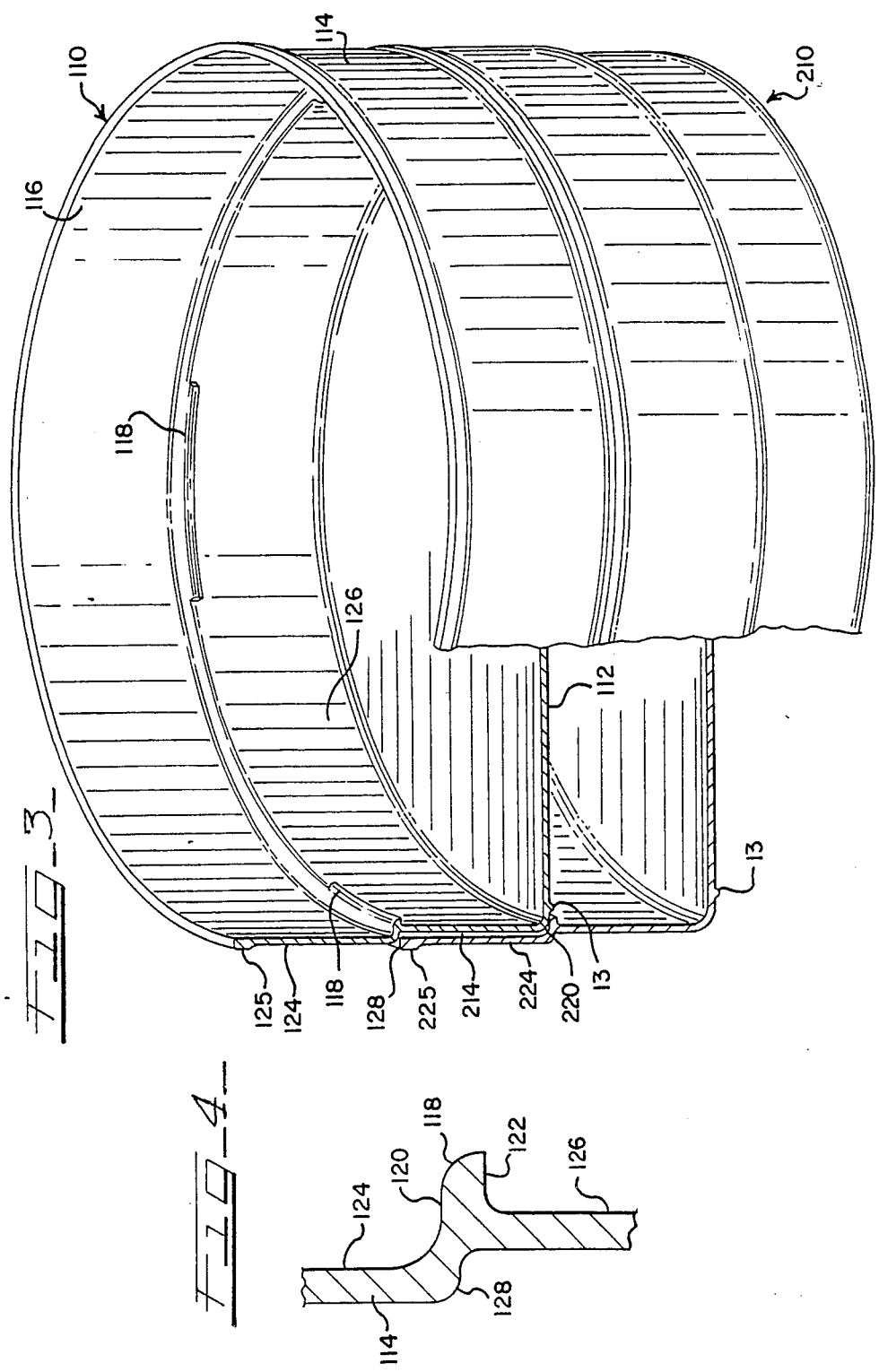

CATHETER BOWL

FIELD OF THE INVENTION

This invention relates to containers for storing medical tubing and in particular to bowls for storing catheters.

Background of Invention

Flexible catheters are often inserted into a patient's body so that fluids can be introduced to the body, removed from the body, or certain examinations can be made. For example, catheters are introduced into a vein so that an examination of internal organs such as the heart can be conducted. Such catheters have outside diameters generally ranging from about 1 to about 3 millimeters. One such catheter known as a J-wire catheter includes a flexible core guide wire.

Before a catheter can be introduced into the body, it is necessary that it be both sterile and wetted with an agent such as saline. The reason for wetting the catheter is to insure that it properly slides through a lumen such as a blood vessel without causing damage. This is most easily done by placing the catheter in a container filled with a saline or sterilizing solution.

Cases for storage of catheters are often included as part of a surgical kit which contains components needed for a particular surgical procedure. Such kits usually consist of an inner tray having a number of compartments sized to store a particular component. In such cases, the catheter is placed in a narrow channel into which the catheter fits.

Several drawbacks are present with such cases. First, such cases are quite bulky due the length and resiliency of the catheter. In addition, such cases are quite expensive due to the costs of fabrication of the case.

In place of a case defining a narrow channel, it has been found that the catheter can be coiled and placed in a bowl to prepare it for use. However, when a bowl is used with a catheter, certain problems can arise. Because the catheter generally resists being curved or bent, there is a tendency for the coiled catheter to lift itself out of the bowl. To reduce this tendency, the bowl is provided with generally vertical sides to limit the tendency of the catheter to lift itself out of the bowl prematurely. However, even vertical sides on a catheter bowl are often not enough. If the catheter is not placed perfectly parallel to the bottom of a bowl, it can still force its way out of the bowl.

Accordingly, what is needed is a means by which a catheter can be easily placed within a bowl in such a way that it will be retained within the bowl without the danger of being prematurely forced from the bowl. Such a catheter bowl should also allow the catheter to be easily removed from the bowl when desired. The catheter bowl should not only provide easy retention of the catheter, but also provide for efficient storage of not only the catheter but the bowl itself. The catheter bowl of present invention meets these desires.

SUMMARY OF THE INVENTION

The present invention relates to a bowl for storage, sterilization or wetting of a catheter for use in the treatment of patients. The catheter bowl has a bottom wall, which is preferably circular, and a continuous side wall extending above the bottom wall. The side wall defines an inner surface which is generally perpendicular to the bottom wall to help retain the catheter within the catheter bowl. The side wall and bottom wall together define the interior of the bowl.

To further assist in retaining the catheter within the bowl, an inwardly extending retaining member is integrally provided on the continuous side wall. The retaining member defines a lower edge to engage and retain the catheter within the bowl. The lower edge preferably extends outwardly from the side wall at an angle of incidence of about 90 degrees. The retaining member thus securely retains the catheter in the bowl while providing for easy insertion and removal of the catheter to and from the bowl.

In the preferred embodiment, a plurality of retaining members are located around the inner surface of the side wall. It is preferred that the retaining members generally occupy more than about one-third of the inside circumference of the side wall. It is also preferred that the retaining members extend into the interior space by an amount greater than one-half of the catheter diameter, but generally less than or equal to the diameter of the catheter itself. This combination provides for particularly effective maintenance of the catheter within the catheter bowl while allowing for easy insertion and removal of the catheter. This configuration also provides for particularly sturdy or retaining members of which do not easily break off or which do not extend so far into the catheter bowl as to possibly injure the fingers of the user.

In a preferred embodiment, the side wall includes a bottom portion adjacent the bottom wall, a top portion of larger cross sectional area than the bottom portion and a step between the top and bottom portions. The interior space defined by the top portion is preferably of a larger diameter than the exterior diameter of the bottom portion. This allows the bowl to be nested with other corresponding bowls thereby simplifying storage of both bowls and catheters.

BRIEF DESCRIPTION OF THE DRAWINGS

FIG. 1 is a perspective view of one embodiment of a catheter bowl in accordance with the present invention;

FIG. 2 is an enlarged cross-sectional view of the embodiment of FIG. 1 taken along plane 2—2 of FIG. 1 showing a retaining member of the catheter bowl;

FIG. 3 is a perspective view, partially broken away, of an alternative embodiment of two catheter bowls of the present invention, shown nested together; and FIG. 4 is an enlarged cross sectional view of the side wall of one of the catheter bowls shown in FIG. 3.

DETAILED DESCRIPTION OF A PREFERRED EMBODIMENT

Referring to FIGS. 1 and 2, a catheter bowl in accordance with the present invention is designated generally by the reference number 10. The catheter bowl 10 includes a bottom wall 12 and a continuous side wall 14 having an inner surface 16 which is generally perpendicular to the bottom wall. Extending from the bottom wall 12 a rim 13 (best seen in FIG. 4) can be provided which supports the catheter bowl 10 when on a flat surface. While in the described embodiment the catheter bowl 10 is preferably circular, other shapes capable of retaining a coiled catheter such as oblong are also possible with the present invention.

The continuous side wall 14 can be formed integrally with the bottom wall 12 preferably by injection molding with a suitable plastic. While the use of any suitable plastic is contemplated, polypropylene or any similar plastic having a good degree of resilience is particularly suited for the present device. Such resilience reduces the likelihood of breakage of the bowl while in use. Direct molding of the catheter bowl also allows a wide range of materials to be used.

The inner surface 16 of side wall 14 is generally perpendicular to bottom wall 12 so that the coiled catheter is not urged upward by the shape of the side wall 14. An angle substantially greater than perpendicular, in conjunction with the forces of the coiled catheter will force the catheter upwardly away from the bottom wall. Since it is preferred to keep the catheter generally toward the bottom wall and within any solution contained in the catheter bowl, such movement of the catheter is to be avoided.

An inwardly extending retaining member 18 is provided on the inner surface 16 of the side wall 14 to further help retain the catheter within the bowl. The retaining member 18 can extend continuously around the inner surface 16 of the side wall 14 as a flange, or preferably, a plurality of intermittent retaining members 18 are spaced about on the inner surface 16 of the side wall 14. The retaining members 18 preferably maintain the same cross section when viewed as in FIG. 2 about the inner surface 16 of the bowl.

Where a plurality of retaining members 18 are used, their combined length about the inner surface 16 should be greater than about one-third of the distance around the inner circumference. For example, as shown in FIG. 1, the retaining members 18 are shown with a combined total length of about one-half the distance around the inner surface. Thus, each of the three retaining members has a length of about 1/6th of the inside circumference with the distance between retaining members being about 1/6th of the inside circumference along the inner surface 16. The retaining members 18 are preferably spaced equal distant about the inner surface. This provides efficient retaining of the catheter within the bowl while minimizing the distance that the retaining member 18 must extend into the bowl. The spaces between the retaining members allow the catheter to be easily inserted and removed.

In the preferred embodiment, the retaining members 18 are integrally molded with the side wall 14. Such integral molding is particularly advantageous over prior art devices which utilize separate, secured retaining members because integral molding avoids the difficulties of permanently attaching the support member and the limitations of materials suitable for such attaching. Integral molding also avoids any cracks or crevices into which foreign matter may collect, thus allowing efficient and thorough cleaning of the bowl.

When placed within the bowl, the coiled catheter has an energy potential as a result of its natural resiliency. Particularly if the coiled catheter is not parallel to the bottom wall as opposed to being cocked at an angle, this energy potential can act to urge the catheter toward the top of the bowl. The retaining member 18 thus engages the catheter and acts to hold the coiled catheter in the bowl to prevent accidental exiting of the catheter.

By utilizing the retaining members 18, the present invention avoids the use of a narrow linear channel into which the catheter fits. Because elongated catheters can be in excess of three feet in length (about one meter), devices in the prior art which utilize catheter channels can become quite bulky. The present device can easily handle catheters in excess of three feet in length (about one meter) with a side wall diameter as of, for example, eight inches (about twenty centimeters).

Referring now to FIG. 2, a cross-sectional view of one of the retaining members 18 is best seen. The retaining member 18 is preferably provided integrally with the side wall 14, preferably in the same injection molding process. The retaining member 18 includes an upper edge 20 which preferably extends gradually from the side wall at an angle from the side wall greater than about 90 degrees. As shown, the upper edge 20 is preferably rounded. This enables the coiled catheter to easily slide past the retaining member 18 into the bottom portion of the bowl for storage.

The retaining member 18 also includes a lower edge 22 which preferably extends perpendicular from the side wall at an angle from the side wall of about 90 degrees. This edge 22 keeps the coiled catheter in place. The retaining member 18 preferably extends into the catheter bowl, by an amount of at least one-half of the diameter of the catheter which will be used. That way, the edge 22 has a width of at least one-half the diameter of the catheter and preferably less than or equal to the diameter catheter. This helps retain the catheter within the catheter bowl 10 by avoiding contact of the curved surface of the catheter by the inner-most portion of the edge 22.

The edge 22 need not be greater than the diameter of the catheter, since this does not provide much greater retaining strength for the catheter in the bowl, and instead tends to hamper insertion and removal of the catheter to and from the bowl. The retaining members 18 preferably extend about 1 to about 3 millimeters to the bowl 10 from the inner surface of the side wall 14. The length of the retaining member 18 along the inner surface 16 in conjunction with the width of the edge 22 combine to provide effective retaining power while permitting easy insertion and removal from the catheter bowl.

Referring to FIGS. 3 and 4, an alternative preferred embodiment for the catheter bowl 110 is shown. As before, the side wall 114 extends generally perpendicular from the bottom wall 112. In this embodiment, the retaining member 118 again includes a lower edge 122 which preferably extends sharply from the side wall 114 and an upper edge 120 which preferably extends gradually from the side wall 114.

In this embodiment, the side wall 114 includes a bottom portion 126, a top portion 124 of larger cross sectional area than the bottom portion, and a step 128 between the top portion and the bottom portion. The portions of the side wall 114 are preferably cylindrical and accordingly, the step 128 preferably has a annular cross section.

In this embodiment, the retaining members 118 are positioned on the side wall 114 adjacent the step 128 and between the top portion 124 and the bottom portion 126 of the side wall. The diameter of the top portion 124 is larger than the diameter of the bottom portion 126, preferably larger by a sufficient amount such that the bottom portion 126 of one bowl 110 fits inside the top portion 224 of a second bowl 210 as shown in FIG. 3. The step 128 is preferably formed integrally with the bottom portion 126, the top portion 124, and the retaining member 118. This step 128 can preferably extend from the top portion 124 at an angle greater than about 90 degrees to enable the catheter to easily slide into the bottom of the bowl 110.

The size difference of the two portions enables the catheter bowl 110 of the second embodiment to nest in a corresponding catheter bowl 210. When nested, the heights of the top portion 124 and bottom portion 126 are preferably such that the bottom wall 112 of the first catheter bowl engages the upper edge 220 of the corresponding catheter bowl 210 and a ridge 225 on the top of the side wall 214 engages against the step 128 at its outer diameter, as seen in FIG. 3. This allows stacking or nesting of a plurality of the catheter bowls while maintaining the desired angle of incidence between the bottom wall and the side wall. Having the two catheter bowls 110 and 210 engaging each other at two locations when nested also reduces a possible warpage of the catheter bowls due to pressure that would otherwise be placed at a single location.

By way of example, the catheter bowl 110 of the present invention can have a diameter of about 8 inches (27 centimeters) and still retain catheters of greater than one meter in length. Preferably, the overall height of the catheter bowl can be approximately 3 inches (7.6 centimeters) with the respective heights of the top portion 124 and bottom portion 126 each being approximately one-half of the total height, namely each being about 1.5 inches (3.8 centimeters) in height. As shown, the retaining members 118 extend into the catheter bowl approximately 0.1 inches (2.5 millimeters) with a total of 4 retaining members being preferred. The retaining members 118 should cover approximately ½ of the inside circumference of the catheter bowl. In the case of polypropylene, it has been found that effective results and efficient molding of the catheter bowl can be achieved with the retaining members extending this distance from the inner surface of the bottom portion. This provides a sturdy catheter bowl which can be easily manufactured, but is still sufficiently sturdy for continuous use for many years.

In molding the preferred embodiments disclosed herein, care must be used to preserve several advantageous features of the preferred embodiment. The retaining members 18 are preferably integral with the side wall 14 which in turn is generally perpendicular to the bottom wall 12. To alleviate the problem of back draft, the preferred embodiment described can be made by injection molding with a mold that includes a collapsible core.

The use of such collapsible core further enables a lengthening of the width of the retaining members 18 to either a continuous member or a plurality of members which leave only about half of the circumference of the inner surface 16 not covered by such members. This is preferable to the use of numerous narrow, inwardly extending knobs acting as the retaining members. Longer retaining members are more likely to be broken or sheared off as narrow members. The present design reduces the distance the members must extend inwardly to hold the catheter in place and makes user injury on the inwardly extending members less likely. In practice, it has been found that such long retaining members utilizing an angle of incidence of about 90 degrees from the side wall 14 and extending inwardly just over half the diameter of the catheter satisfactorily hold the catheter in the bowl.

The catheter bowl can be utilized in variety of ways. The bowl itself can be distributed to be used by medical personnel with a separately supplied catheter. The catheter is slid into place for storage and sterilized by such means as a sterile wash. The bowl can also be distributed with a lid and a catheter already in place, with the package sterilized and sealed. Finally, the catheter bowl can be utilized as a part of a catherization package with additional compartments of a tray to contain any additional catherization implements.

It should be understood that various modifications, changes, and variations may be made in the arrangement, operation, and details of construction of the elements disclosed herein without departing from the spirit and scope of the invention.

What is claimed is:

1. A bowl for providing storage of a catheter comprising:
    a bottom wall;
    a continuous side wall having an inner surface generally perpendicular to the bottom wall; and
    an inwardly extending retaining member integrally molded on the inner surface of the side wall and defining a lower edge for engaging the catheter.

2. The bowl of claim 1 wherein the side wall has a bottom portion adjacent the bottom wall, a top portion of larger cross-sectional area than the bottom portion and a step between the top and bottom portions.

3. The bowl of claim 2 wherein the top portion has an interior surface which defines a cross-section greater than a cross-section of an exterior surface of the bottom portion.

4. The bowl of claim 3 wherein the bottom portion of the bowl is nestable within the top portion of a corresponding bowl.

5. The bowl of claim 1 wherein the lower edge of the retaining member has an angle of incidence from the side wall of about 90 degrees.

6. The bowl of claim 1 wherein the bowl is nestable with a bowl of the same general configuration.

7. The bowl of claim 1 including a plurality of retaining members spaced about the inner surface of the side wall.

8. The bowl of claim 7 wherein the retaining members extend over at least one-third of the inner circumference of the side wall.

9. The bowl of claim 1 wherein the retaining member extends about 1 to about 3 millimeters from the inner surface of the side wall.

10. The bowl of claim 2 wherein the retaining member is adjacent the step.

11. The bowl of claim 7 wherein the retaining members are spaced equidistant from each other about the inner surface of the side wall.

12. The bowl of claim 1 wherein the retaining member extending from the side wall has a rounded upper edge.

13. The bowl of claim 1 wherein the retaining member extends inwardly at least half of the diameter of the catheter.

14. A bowl for providing storage for a catheter comprising:
    a generally circular bottom wall;
    a side wall having a generally cylindrical bottom portion defining an inner surface generally perpendicular to the bottom wall, a generally cylindrical top portion having a larger diameter than the bottom portion, and a generally annular step between the top portion and the bottom portion; and
    an inwardly extending retaining member integrally molded on the inner surface of the bottom portion of the side wall, the top portion being sufficiently larger than the bottom portion to enable a bottom portion from a second corresponding bowl to nest in the top portion of the bowl.

15. The bowl of claim 14 wherein the inwardly extending retaining member defines a lower edge having an angle of incidence from the bottom portion of the side wall of about 90 degrees.

16. The bowl of claim 14 including a plurality of retaining members spaced about the inner surface of the side wall.

17. The bowl of claim 16 wherein the retaining members extend over at least one-third of the inner circumference of the side wall.

18. The bowl of claim 17 wherein the retaining members extend about 1 to about 3 millimeters from the inner surface of the side wall.

19. The bowl of claim 14 wherein the retaining member extends inwardly at least half of the diameter of the catheter.

20. The bowl of claim 14 wherein the respective heights of the top and bottom portions are such that when two catheter bowls are nested together to the bottom of the top bowl engages the step of the second bowl while the step of the first bowl engages a top ridge defined by a top portion of the side wall of the second bowl.

21. The bowl of claim 16 wherein the retaining members are spaced equidistant from each other about the inner surface of the side wall.

22. The bowl of claim 14 wherein the retaining member extending from the side wall has a rounded upper edge.

23. A bowl for providing storage for a catheter comprising:
a generally circular bottom wall;
a side wall having a generally cylindrical bottom portion defining an inner surface generally perpendicular to the bottom wall, a generally cylindrical top portion having a larger diameter than the bottom portion, and a generally annular step between the top portion and the bottom portion, the side wall and bottom wall being integral; and
a plurality of inwardly extending retainer members integrally molded on the inner surface of the bottom portion and spaced equidistant from each other about the inner surface of the side wall adjacent the step, the retaining members extending from the inner surface about 1 to about 3 millimeters, the top portion being sufficiently larger than the bottom portion to enable a bottom portion from a second corresponding bowl to nest in the top portion of the bowl.

24. The bowl of claim 23 wherein the inwardly extending retaining members each define a lower edge having an angle of incidence from the bottom portion of the side wall of about 90 degrees.

25. The bowl of claim 23 wherein the retaining members extend over at least one-third of the inner circumference of the side wall.

26. The bowl of claim 23 wherein the retaining member extending from the side wall has a rounded upper edge.

27. The bowl of claim 23 wherein the retaining members extend inwardly at least half of the diameter of the catheter.

* * * * *